US006689621B2

(12) United States Patent
Merten et al.

(10) Patent No.: US 6,689,621 B2
(45) Date of Patent: Feb. 10, 2004

(54) FLUID DISPENSING SYSTEM AND VALVE CONTROL

(75) Inventors: C. William Merten, Dayton, OH (US); Thomas M. O'Brien, New Lebanon, OH (US)

(73) Assignee: Liquid Logic, LLC, Miamisburg, OH (US)

( * ) Notice: Subject to any disclaimer, the term of this patent is extended or adjusted under 35 U.S.C. 154(b) by 364 days.

(21) Appl. No.: 09/725,594

(22) Filed: Nov. 29, 2000

(65) Prior Publication Data

US 2002/0064880 A1 May 30, 2002

(51) Int. Cl.[7] .............................. G01N 1/10; G01N 1/00; B01L 3/02; B01L 11/00; B01L 15/06; B32B 27/04; B32B 27/12

(52) U.S. Cl. .................. 436/180; 436/174; 422/100; 422/103; 422/105; 422/68.1; 422/67

(58) Field of Search ................... 422/100, 103, 422/105, 62, 63, 67, 68.1; 436/174, 180

(56) References Cited

U.S. PATENT DOCUMENTS

| | | | |
|---|---|---|---|
| 3,491,369 A | 1/1970 | Debbrecht | |
| 4,212,845 A | 7/1980 | Stelling et al. | |
| 4,253,846 A | 3/1981 | Smythe et al. | |
| 4,512,953 A | 4/1985 | Marsoner et al. | |
| 4,517,302 A | 5/1985 | Saros | |
| 4,691,850 A | 9/1987 | Kirschmann et al. | |
| 4,725,407 A | 2/1988 | Usui et al. | |
| 4,789,014 A | 12/1988 | DiGianfilippo et al. | |
| 4,860,779 A | 8/1989 | Whitford | |
| 4,967,811 A | 11/1990 | DiGianfilippo et al. | |
| 5,056,568 A | 10/1991 | DiGianfilippo et al. | |
| 5,134,079 A | 7/1992 | Cusack et al. | |
| 5,230,863 A | 7/1993 | Salpeter | |
| 5,268,147 A | 12/1993 | Zabetakis et al. | |
| 5,399,497 A | 3/1995 | Kumar et al. | |
| 5,464,121 A | 11/1995 | Jones | |
| 5,504,010 A | 4/1996 | Mitani et al. | |
| 5,583,790 A | 12/1996 | Lan et al. | |
| 5,823,234 A | 10/1998 | Boertz | |
| 5,826,749 A | 10/1998 | Howland et al. | |

FOREIGN PATENT DOCUMENTS

GB        2 185 569 A        7/1987

*Primary Examiner*—Jill Warden
*Assistant Examiner*—Brian R. Gotdon
(74) *Attorney, Agent, or Firm*—Dinsmore & Shohl

(57) ABSTRACT

An apparatus for the control of fluid flow through a valve. A single shaft-mounted cam moves translationally along the length of the shaft, stopping sequentially at positions adjacent to and in operative engagement with an actuator disposed on or near a valve body. Once in position with a predetermined valve, the cam, which is also coupled to a rotational member, is rotated, thus causing an eccentric portion of the cam to engage the actuator in such a way so as to force the valve to open or close. A flow detection system is integrated into a main fluid transport conduit, allowing sensed flow variations to be sent to a controller. The controller uses a comparison algorithm to determine what fluid settings in the valve are necessary to effect a desired fluid flow through the valve, and prepares an input signal to be sent to one or more motors controlling the translational and rotational motion of the cam. Capping devices and an enclosure with a safety door can be included to protect personnel and the ambient environment against fluid spillage.

33 Claims, 7 Drawing Sheets

FLUID DISPENSING SYSTEM AND VALVE CONTROL

BACKGROUND OF THE INVENTION

The present invention relates generally to a fluid dispensing system with a device for controlling the flow of fluids through a plurality of valves, and more particularly to a shaft-mounted cam that through a combination of translational and rotational motion can sequentially open or close one or more valves to precisely control the ratio of fluids added to a fluid mixture.

The use of valves and valve actuators to control the flow of gases and liquids in a fluid combining process or system is well known in the art. One area where precise actuation and control of the valves is critical is in chemical processes, where a large number of valves are employed, often in an extensive array of piping, conduit, ducting or related fluid carrying and containing equipment. The attendant level of monitoring and process control necessary to ensure that these larger, more complex valving systems are performing their intended tasks has rendered manual control of such systems difficult. In response, automated valve control was developed, and with the advent of computer-controlled systems, even more sophisticated ways to control and monitor any given chemical process have become commonplace. While the more precise, predictable control over valve closure and opening associated with automated devices has enabled improved system functionality, it has come with system cost, weight and complexity burdens.

Many of today's modern chemical processes, including oil or petroleum refining, food and drug manufacturing and electric generation, rely extensively on the complex interconnection of pumps, piping and valves to effect a particular chemical conversion or mixture. One of the more frequently used forms of chemical processing involves the use of a fluid dispensing system, wherein a single fluid transport conduit permits multiple fluids to be selectively injected into a main stream to create a final mixed product for dispensing. However, there are situations in which fluid dispensing systems, although potentially beneficial, have not found application. One example is the preparation of etchants for metals in the metallurgical laboratory. They are usually prepared in small quantities (typically 100 ml or less), and owing to their reactivity with metals are corrosive and hazardous by nature. Typically, these etchants are recipes comprising a mixture of constituents formulated to react with a given metal. As such, precise control over the ratios to ensure a quality etchant mixture is necessary. While such precise control with prior art systems embodying fluid dispensing features is possible, their reliance on multiple dedicated pumps or redundant valve and actuator engaging configurations results in complex, expensive systems that require that each actuator must be equipped with numerous dedicated devices in order to control multiple valves.

Another especially acute problem involves the precise control of minute quantities of fluids. When small quantities of injectants are being mixed, such as with medicament samples, acid etchants and related chemical reagents, the lack of a simplistic fluid dispensing system, which can meter precise amounts of the desired fluids reliably, affordably and safely is a hindrance to the creation of application-specific fluids. In response to ever-increasing demands that end product mixtures be of extremely high quality, with minimal contamination, waste and risk of exposure of personnel or the environment to hazardous substances, existing systems have added backup and redundant componentry, exacerbating system cost and complexity. Depending on the size of the fluid transport conduit in a fluid dispensing system, the driver fluid in the conduit's main stream could be either a conventional liquid (most notably water) carrier or an immiscible gas (most notably air) being drawn into the main stream through a supply valve. With a liquid-based driver system, a "pusher" fluid is used to move the injectant through the main stream of the conduit and into the dispensing unit. By using an "all liquid" approach (i.e.: liquid pusher and liquid injectant), the potential for an extremely accurate final mixture exists, due in part to the incompressibility of the liquids. However, the present inventors have discovered that the size of the conduit effects the mixing process. If the conduit is too large, the discrete volume of fluid in the conduit tended to collapse and mix with the pusher fluid. Likewise, if the size of the conduit is too small (as can be the case when small quantities of injectant are used), friction effects can dominate, resulting in slow dispensing speeds and higher power requirements.

In metallurgical laboratories, metallurgists and metallurgical technicians routinely prepare etchants, mixtures of acids, solvents, and salts, which are used to etch metallographic samples, thus revealing microstructure and other features. The preparation of etchants, as it is currently practiced in the metallurgical lab, entails: the transfer of acids and solvents from the bottles in which they are supplied to smaller containers to facilitate handling; the measurement of volumetric quantities of these acids and solvents using graduated cylinders; and the mixing of the same in a container along with mass quantities of salts, if required. The handling and measurement activities are time consuming and entail significant risk to both personnel and the environment. Alternatively, some laboratories transfer acids and solvents from the containers in which they were purchased into an individual dispenser for each reagent, or insert a bottle top dispenser into each bottle in which a reagent is purchased. After the etching operation is completed, the etchant must be neutralized prior to disposal. Many laboratories perform the pH neutralization procedure with sodium hydroxide pellets. Because sodium hydroxide is highly reactive in acid, as are related acid neutralizers, it must be added slowly to minimize foaming and spatter. Personnel performing this operation check the neutralization process frequently using litmus paper to determine the pH of the solution. This can be tedious, time-consuming, and potentially dangerous to personnel, adjacent laboratory equipment and the ambient environment. In addition, it is frequently the case that too much neutralizer is added, thus necessitating the addition of more acid in an ad hoc process to ensure that an acceptable pH (typically in the range of 6 to 8) is reached prior to disposal. Not only does the prolonged exposure due to this back-and-forth process present additional risks to personnel, equipment and the environment, but it generates additional quantities of waste product as well.

Other applications for a fluid dispensing system capable of handling acids and solvents exist outside of the metallurgical laboratory. One example is compositional analysis of metals in the chemical laboratory using a technique known as inductively coupled plasma. Prior to analysis, the metal to be analyzed must be placed in liquid solution. To accomplish this, chemists dissolve the metallic sample in mixtures of acids and solvents similar to etchants. In the chemical laboratory, the preparation, neutralization and disposal of these solutions of acids and solvents proceeds in much the same way as it does in the metallurgical laboratory.

Similarly, in other contexts, examples of commercially available systems exist in which a peristaltic pump is devoted to each liquid to be dispensed. Such systems may be combined with valve manifolds to redirect liquids to a plurality of locations. Valves in such manifolds are generally activated individually using electromechanical devices such as solenoids. Other commercially available systems use multiple screw driven syringes or multiple syringe pumps to dispense a multiplicity of liquids. In any event, exposure to harsh chemicals can present safety and operability risks that typically require additional costs associated with redundant, protective system componentry.

Accordingly, there exists a need for a fluid dispensing system that can offer greater simplicity, improved safety to using personnel, improved conservation of constituent fluids, and greater speed of fluid mixture preparation.

SUMMARY OF THE INVENTION

This need is met by the present invention by providing a simple, reliable means for controlling the opening and closing of multiple fluid insertion valves arranged in a common valve manifold without having to rely on the use of complicated, redundant actuators. The current invention preferably employs a cam which can be translated by means of a lead screw across a linear array of valves and rotated to actuate a given valve when located in juxtaposition to that valve. By placing a single pump upstream of the valve manifold and a dispensing nozzle downstream, the multiplicity of pumps can be eliminated. The inventors of the present invention have further recognized that their approach increases throughput of the dispensed final product while avoiding the complexity and redundancy of larger, heavily-arrayed fluid transport conduit systems. One of the chief attributes to the system of the present invention is that by using a single cam on a single shaft as a valve actuator engaging member, thus resulting in a single translation member and a single rotation member, the device is inherently simple and compact. Further system simplicity is ensured by the use of one or more conventional motors to move the cam, such as a stepper motor, servomotor or rotary solenoid. Alternatively, the use of multiple pumps of different sizes could be employed to achieve high volumetric accuracy when small amounts of reagent are to be injected into large amounts of solution. In this case pumps with different capacities may be plumbed either in parallel or in series in such a way that the smaller pump provides greater accuracy during aspiration where as the larger pump provides greater capacity during aspiration and greater speed during dispensing.

In accordance with one embodiment of the present invention, a fluid dispensing system (also known as an injectant dispensing system) is disclosed. It includes at least one pump for metering precise quantities of fluid to be dispensed; one or more fluid injection lines for transporting a fluid to be dispensed, and one or more valves with valve actuators, each of the valves disposed in one of the fluid injection lines, wherein the fluid injection lines can be in fluid communication with fluid dispensing containers at one end, and with a fluid transport conduit at the other. The fluid transport conduit is also in fluid communication with the pump. Each of the valves can control the flow of a quantity of fluid through one of the fluid injection lines. At least one valve actuator engaging member is coupled to each of the valve actuators so that, based on a control signal, each actuator engaging member can force a respective actuator on the valve to open or close the valve in response to the control signal. Furthermore, a pusher fluid is selectively introduced into the fluid transport conduit to force the flow of a fluid to be dispensed through the fluid transport conduit. In the present context, a pusher fluid is one used as a carrier, such that it moves the injectant fluid through the fluid transport conduit and into the pump. The choice of a particular pusher fluid can effect the way many of the system elements are interconnected. Specifically, the size of the fluid transport conduit, pump size and type can be tailored to the dispensing of small quantities of fluids to minimize or prevent fluid intermixing and residual droplet formation. In addition, the present inventors discovered that if the pusher fluid is a liquid, an optional filter device can be disposed in the pusher fluid injection line to not only reduce contaminant presence but also provide damping for flow stability. A flow detection system is disposed adjacent the fluid injection lines, and includes at least one detector and a controller in electrical communication with the detector, valves and pump such that upon detection and comparison of a flow variation, the controller sends signals to at least one of the pump or valves to control the flow of fluid. This system is especially well-suited to the use of acids, solvents and acid neutralizers.

Optionally, to meet the need of ensuring that the highly accurate approach of using a liquid pusher with a small bore conduit could be replicated without the aforementioned speed and power drawbacks, the present invention further may include an immiscible gas as the pusher in small conduit lines (such lines being commonly associated with the use of acid reagents for etchant solutions). Thus, by using a gaseous pusher fluid for small mixture quantities, where an appropriate amount of conduit is placed between the pump and the fluid injection valves in the absence of a liquid pusher, the aspiration of the fluid could be accurately metered, resulting in precise mixtures to be dispensed. Advantages of this approach include the use of a smaller, more simplistic fluid transport conduit, as well as reducing the need to dilute or mix the fluid with a water-based main stream carrier. As another option, the fluid dispensing system can include a capping mechanism adapted to be disposed in the container apertures, thus acting as a stopper to prevent unintended release of fluids from the container. Furthermore, the capping mechanism permits the flow of fluid to and from the container under normal operating conditions by being operatively responsive to pressure differentials arising out of putting fluid into and taking fluid out of the container. The capping mechanism, which is operatively responsive to a pressure differential across the aperture in each of the containers, can include the following features: a generally cylindrical body; at least one threaded groove disposed on the body's outer surface such that a complementary threaded top can be fit thereon; at least one recess disposed in an outer surface of the body and axially distant from the threaded groove. The recess is adapted to receive an O-ring to facilitate better sealing as well as easier, safer removal. At least one aperture is disposed therein to receive a fluid injection line. The capping mechanism itself may include at least one elastic vent member with at least one slit and at least one channel disposed therein; and at least one membrane plate with at least one recess and at least one channel disposed therein, where the recess is in substantially axial alignment with the slit. Slits placed in the compliant members can respond to pressure differentials between the inside and outside of the container, which then permits the insertion and withdrawal of fluid. In the alternative, the capping mechanism may include: a plurality of passages; at least one venturi; a plurality of generally spherical stoppers disposed within a chamber in the body such that they are seatably responsive to a pressure differential in the fluid transfer line that extends between the container and the fluid transport conduit, such that, upon exposure to a pressure differential, the generally spherical stoppers change their seating arrangement against the aperture. Another desirable attribute of the present invention is its incorporation of fluid containment devices that permit relatively "handsfree" fluid dispensing system operation of handling acids, solvents and dispensing liquid neutralizer. For example, the inventors discovered that when the mixing process involves hazardous substances, such as acids and related etchants, exposure of the vapors and liquids to personnel and sensitive equipment could be minimized through the use of an appropriate capping mechanism. The features of the capping mechanism permit the uninhibited access of fluid to and from the fluid container while simultaneously minimizing the chance of liquid spillage or inadvertent venting of corrosive or noxious vapors. With the inclusion of features such as this, the present invention greatly increases the efficiency of dispensing and neutralization processes by integrating improved safety features into the dispensing system's inherently simple design. As another option, a filter is disposed in the fluid injection lines to provide fluid damping. Additional options to the flow detection system include specific detector features. For example, the detector can be either an ultrasonic or optical detector, where more specifically, in embodiments using the optical detector, it can be an IR detector. Another option is the inclusion of a neutralizer with integral dye indicator into the fluid dispensing system. The neutralizer comprises a base in liquid solution mixed with a dye indicator. Upon addition to an acidic solution, the pH changes. When the pH range of 6 to 8 is achieved, the solution undergoes an abrupt color change. One example of such a neutralizer is triethanolamine, although other solutions, including sodium hydroxide, can be used. Another option includes an enclosure to house one or more of the various components of the fluid dispensing system such that they are disposed within the enclosure. Preferably, the enclosure contains the pump and valve assembly, and is sized to conveniently fit in a fume hood, or on top of a table designed to house fluid reagents, thus providing a compact, autonomous container for the fluid dispensing system.

In accordance with another embodiment of the present invention, a cam assembly is disclosed. The apparatus comprises a shaft, a rotational member, a cam, and a cam driver. The shaft and rotational member each include an axis of rotation along their respective length. The cam moves in at least two degrees of freedom, where the first is preferably a translational movement operatively responsive to its threaded relationship with the turning shaft, and the second is preferably a rotational movement operatively responsive to the interaction between complementary mating cam and rotational member surfaces. Furthermore, each cam degree of freedom movement is independently responsive to shaft and rotational member motion, caused in turn by the cam driver coupled to the shaft and rotational members. In the present context, "independently responsive" means that even though the cam is coupled to both the shaft and the rotational member, it does not require the simultaneous movement of both to perform its intended function. To take up as little space as possible, that shaft can be disposed concentrically inside a hollow portion of the rotational member, and the cam can be disposed on an outer surface of the rotational member so that the axes of rotation of the shaft, cam and rotational member are coaxial. This space-saving feature is highly desirable in volume-limited applications, such as when working with hazardous substances, where the entire assembly might need to be located in a fume hood or similar device. Moreover, the cam driver need not be a single motor, but instead can comprise a first motor for imparting translational movement to the shaft, and a second motor for imparting rotational movement to the rotational member.

In accordance with another embodiment of the present invention, a flow control apparatus for porting fluids is disclosed. The apparatus comprises a housing and a plurality of valves, in addition to the cam assembly described in the previous embodiment. The housing supports the plurality of valves, as well as the shaft, cam and rotational member. Each one of the valves include a valve actuator, that, on one end, is connected to the valve such that movement of the actuator opens or closes the valve. The other end of the actuator engages the eccentric portion of the cam such that rotational changes in the cam produce changes in the actuator's position. In addition, a flow detection system with at least one ultrasonic or optical sensor may be included, and, in the case of an optical detector, operable in either the IR or visible band. This flow detection system can be integrated into a microprocessor-based controller to ensure accurate and repeatable quantities of mixing fluids are being drawn into the mixing region of the pump from their containers. As with the aforementioned fluid dispensing system, this apparatus is especially well-suited to the use of acids, solvents and acid neutralizers.

In accordance with yet another embodiment of the present invention, a fluid dispensing system is disclosed. The fluid dispensing system comprises, a pump, a fluid transport conduit, a valve assembly and a flow detection system, and a dispensing unit in fluid communication with the valve assembly to accept fluid from the fluid transport conduit. The fluid transport conduit provides a containment path through which the injectant fluids can be circulated. The flow detection system (similar to the previously described fluid dispensing system) is in fluid communication with the fluid transport conduit, as is the valve assembly. The valve assembly contains a plurality of valves, each of which includes a valve actuator. While the valves are designed to be either open or closed, they could optionally be coupled to a feedback-based controller to provide flow rate control. The valve assembly itself comprises a housing, shaft, rotational member, cam and cam driver similar to that of the previous embodiment. Optionally, the fluid dispensing system further comprises at least one container for supplying the injectant, where the container is in fluid communication with the valve assembly and fluid transport conduit. The aperture of the container may have a capping mechanism similar to that described in conjunction with the previous fluid dispensing system embodiment. As with the prior fluid dispensing system embodiment, an enclosure can be included to house one or more of the individual components within the fluid dispensing system. Additionally, the fluid dispensing system includes safety and convenience features, such as a dispensing unit including a dispensing nozzle to facilitate the introduction of fluid in the fluid transport conduit into a receiving container (such as a beaker), a mixing device (such as a magnetic stirrer) to improve mixing of dispensed fluid in the receiving container, a door disposed on the enclosure to prevent fluid spillage from escaping, an interlock that prevents the fluid dispensing system from operating until the door is closed, a drain disposed within the dispensing unit to collect any fluid spillage inside the dispensing unit, a pressure relief valve to protect the fluid transport conduit from becoming overpressurized, and a waste receptacle attached to the drain and pressure relief valve. Optionally, the fluid dispensing system can accommodate various pusher fluids in a fashion similar to that of the previous embodiment fluid dispensing system. Also as with the previous embodiment fluid dispensing system, a neutralizer with integral dye indicator can be added to facilitate efficient neutralization of the dispensed fluids, which can include, among others, acids, solvents and acid neutralizers.

In accordance with still another embodiment of the present invention, a method for controlling the amount of fluid flowing through at least one of a plurality of valves is disclosed. The method comprises the steps of placing at least one fluid container in operative communication with at least one valve, arranging a valve actuator to be in mechanical communication with the valve, mounting a cam to both a shaft and a rotational member such that the cam is operatively responsive to movements in the shaft and rotational members, placing a cam driver to provide translational and rotational movement to the cam through the shaft and rotational member, and controlling the opening or closing of the valve in response to a predetermined process condition. This last step is accomplished by receiving an input from a control mechanism, sending a control signal from the control mechanism to the cam driver, translating the cam until it is aligned with the valve actuator, then rotating the cam to force engagement between it and the valve actuator to open the valve until a desired amount of fluid is injected into the fluid transport conduit. Optionally, the method is accomplished with a device that has the shaft axis of rotation coaxial with the rotational member axis of rotation, and where the control mechanism comprises a microprocessor-based controller. The method may also include installing a flow detection system, whereby air pockets or bubbles injected into either the fluid transport conduit or the fluid injection lines can be sensed, then correlating the sensed value against a predetermined fluid volume to be dispensed, then calculating a flow adjustment signal to send to the cam driver to adjust the valve to remain open for an additional period to ensure adequate quantities of fluid are dispensed. Other features that may be incorporated include an aperture in the fluid container with a capping mechanism such that when the fluid is flowing neither to nor from the container, the capping mechanism prevents the fluid from escaping from the container, as well as to facilitate the flow to or from the container during such periods that fluid transport is necessary. Such capping mechanisms having already been described herein.

In accordance with still another embodiment of the present invention, a method for preparing metallurgical etchants is disclosed. The steps of this method include: placing at least one fluid container with a fluid to be dispensed disposed therein in operative communication with at least one valve; arranging a valve actuator to be in mechanical communication with the valve; placing a fluid injection line in fluid communication with the valve such that the fluid injection line is also in operative communication with the fluid container; placing a fluid transport conduit in fluid communication with the fluid injection line; placing at least one pump for metering precise quantities of the fluid to be dispensed in fluid communication with the fluid transport conduit, thereby establishing fluid communication between the pump and the fluid container; selectively introducing a pusher fluid into the fluid transport conduit to force the flow of the fluid to be dispensed through the fluid transport conduit; monitoring the flow of the fluid to be dispensed through the fluid injection line with a flow detection system; controlling the opening or closing of the valve in response to a predetermined process condition by receiving an input from the controller, and sending a control signal from the controller to the valve actuator, thereby forcing engagement between the valve actuator and the valve to an extent dictated by the control signal such that the valve adjusts a flow of the fluid to be dispensed; and operating the pump to move a predetermined amount of the fluid to be dispensed from the fluid container, through the valve, fluid injection line, fluid transport conduit, and into a dispensing unit in fluid communication with the fluid transport conduit so as to accept fluid therefrom. The flow detection system itself comprises at least one detector placed in sensor communication with the fluid injection line and a controller in electrical communication with the detector, valve and pump such that upon detection and comparison of a flow variation, the controller sends signals to at least the pump or valve to control the flow of the fluid to be dispensed. Optionally, the fluid to be dispensed by the method is an acid, solvent or acid neutralizer. The method may further include a step to neutralize the etchant after use by dispensing an acid neutralizer with an integral dye indicator contained therein to indicate when a desired pH level is attained. This step could obviate the need to iteratively adjust the pH of the spent etchant.

In accordance with still another embodiment of the present invention, a method for preparing metallurgical etchants is disclosed, comprising the steps of: placing at least one fluid container with a fluid disposed therein in operative communication with at least one valve of a plurality of valves; arranging a valve actuator to be in mechanical communication with the valve; mounting a cam to both a shaft with an axis of rotation along its length and a rotational member with an axis of rotation along its length such that the cam is independently responsive to rotation of the shaft and rotational member; placing a cam driver for translating and rotating the cam relative to the valve in operative communication with both the shaft and rotational member; and controlling the opening or closing of the valve in response to a predetermined process condition. The step of controlling includes the following: receiving an input from a control mechanism; sending a control signal from the control mechanism to the cam driver; translating the cam until the cam is aligned with the valve actuator; and rotating the cam to force engagement between it and the valve actuator to an extent dictated by the control signal such that the valve actuator forces the valve to adjust a flow of the fluid therethrough. Optionally, the fluid to be dispensed is an acid, solvent or acid neutralizer, where the neutralizer can include an integral dye indicator.

Other features and advantages of the invention will be apparent from the following description, the accompanying drawings and the appended claims.

BRIEF DESCRIPTION OF THE DRAWINGS

The following detailed description of the preferred embodiments of the present invention can be best understood when read in conjunction with the following drawings, where like structure is indicated with like reference numerals and in which.

DESCRIPTION OF THE PREFERRED EMBODIMENTS

Figure 1:
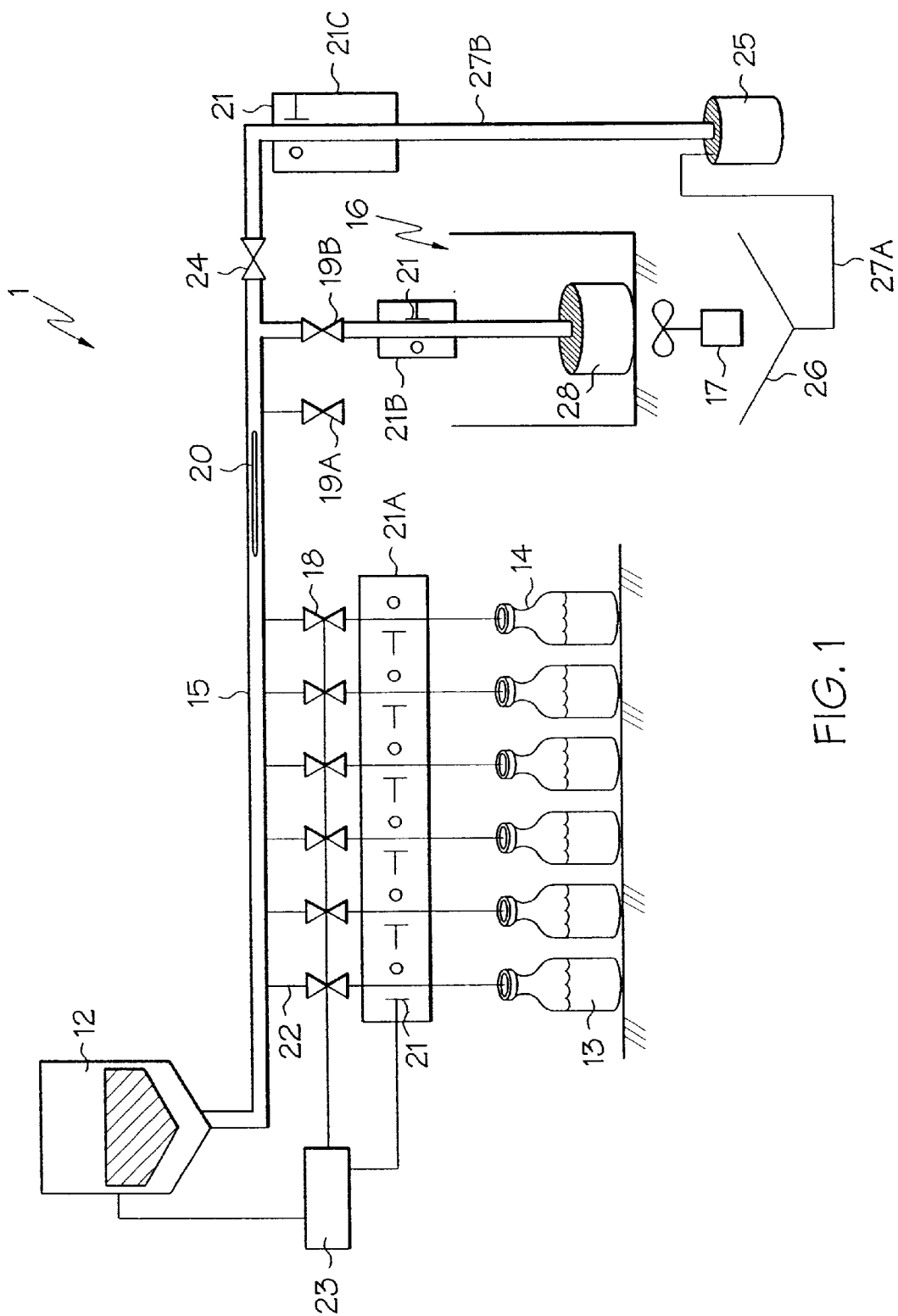
FIG. 1 is a schematic of a general fluid flow path according to an embodiment of the present invention.

Referring first to FIG. 1, a general flowpath for a continuous fluid flow system 1 is shown. Pump 12 moves a reagent (comprising a mixture of individual fluids 13, each of which are stored in container 14), through a conduit 15 to a fluid dispensing unit 16, which holds a fluid receptacle 28. Preferably, pump 12 is a metering syringe pump powered by a stepper motor (not shown), wherein during the suction phase, it draws fluid 13 out of container 14 into fluid injection line 22, past a valve 18. This process is repeated with as many fluids as is necessary to achieve the desired mixture. Once this is accomplished, pump 12 then pumps the mixture into the main stream of conduit 15. Once the fluid is dispensed into fluid receptacle 28, it is mixed, preferably through a magnetic stirrer 17. A series of valves 18 are employed to control the introduction of fluids 13 into conduit 15.

One or more flow sensors 21 (alternately referred to as detectors) are used in various locations in the flowpath to detect fluid flow. Sensor 21 works by sensing the presence of air pockets, either inherently present in the conduit 15 or fluid injection line 22, or in the form of injected bubbles 20. Preferably, the sensor includes a detector and a signal transmitter, both of which are mounted to a common board, such as a printed circuit board (PCB) 21A, 21B and 21C, where PCBs 21A, 21B and 21C are adapted to fit around the fluid injection lines 22, conduit 15 or pressure relief tube 27B, depending on the application. Although the sensors 21 are shown notionally mounted to three separate PCBs 21A, 21B and 21C, they could also be mounted to a single elongate PCB (not shown). In the present invention, sensors 21 may be either ultrasonic, optical, or any other type of device capable of sensing flow changes and converting the sensed signal into a machine or human readable flow number. One suitable optical sensor includes light- or infrared-emitting diodes (LEDs and IREDs, respectively) arranged to transmit a signal to a phototransistor. Although the sensors could also be used to monitor flow rate, it is for measuring discrete quantities of fluid to be injected that they find their primary use in the present invention. For example, each cycle of metering pump 12 (which may be controlled by the aforementioned stepper motor) is designed to suction a precise quantity of fluid 13 present in fluid injection line 22. However, the presence of air pockets (not shown) in the fluid injection line 22, which is indiscriminately drawn up into the pump 12 for mixing, can result in less than the desired quantity of fluid 13 to be drawn up into pump 12 for mixing. The presence of sensors 21 on PCB 21A is designed to prevent these inaccuracies by permitting the density, frequency or spacing of these air pockets within the fluid injection line 22 to be detected, then correlated with the amount of fluid 13 to be aspirated through the use of an automated feedback control arrangement, which is usually a microprocessor-based device such as controller 23. The automated feedback control arrangement will typically utilize algorithms to detect the presence of air pockets in the fluid injection line 22 picked up by sensors 21 on PCB 21A. This precise interactive control of the fluid metering components ensures reliable, highly repeatable resulting mixtures.

A bubble injection mechanism controls, via bubble injection valve 19A, the introduction of bubbles 20 of an immiscible gas, such as air, into conduit 15 to provide thorough and precise quantities of the mixed reagent being discharged from pump 12. It is noted that in the event a liquid "pusher" is desired over an immiscible gas, the bubble injection valve 19A (or an equivalent) could be utilized, preferably in the same general location. Similarly, if a liquid pusher is used, a filter device can be added to ensure that particulate contamination is not introduced into the mixed reagent, as well as providing damping benefits to ensure proper fluid injection, mixing and transport. Sensor 21 mounted to PCB 21B can be used to detect flow of fluid 13 from container 14. In another adaptation, sensor 21 can be mounted to PCB 21C to detect the presence of any flow through pressure relief tube 27B and valve 24 into waste receptacle 25. Bubbles 20 can provide, in addition to a "pusher" fluid to move fluid 13, contamination reduction features, which due to the scrubbing action of bubbles 20 as they traverse conduit 15 remove fluid droplets from the line that could contaminate a subsequent mixture, as well as optional flow rate measuring capability, as previously mentioned. In performing their flow measuring function, the bubbles 20 are first injected by bubble injection valve 19A into the conduit 15 upstream of the location where the fluid reagents 13 are to be inserted. One or more of the sensors 21 are placed downstream of the reagent insertion location, such as on PCB 21B, and usually through either optical or sonic means, detects the flow rate based on the bubble flux. The sensor 21 sends a signal, typically in the form of a voltage, to a controller 23 for comparison to a predetermined flow constant. Based on a comparison of the measured flow rate with the flow constant, the controller 23 can provide active feedback to determine how much and how fast fluid reagent should flow through the main stream of the conduit 15, and then into either fluid receptacle 28 or waste receptacle 25 through pressure relief valve 24, which is included as a system safety measure. Drain 26 and waste tube 27A are situated on a lower surface of fluid dispensing unit 16 to ensure that any spilled fluid is also routed to waste receptacle 25. Dispensant control valve 19B is coupled to the controller 23 (coupling line not shown to minimize drawing complexity) to ensure that reagent is isolated from fluid receptacle 28 during periods where pressure relief valve 24 is activated. Similarly, dispensant control valve 19B is closed when pump 12 is aspirating liquids during its suction phase.

Figure 2:
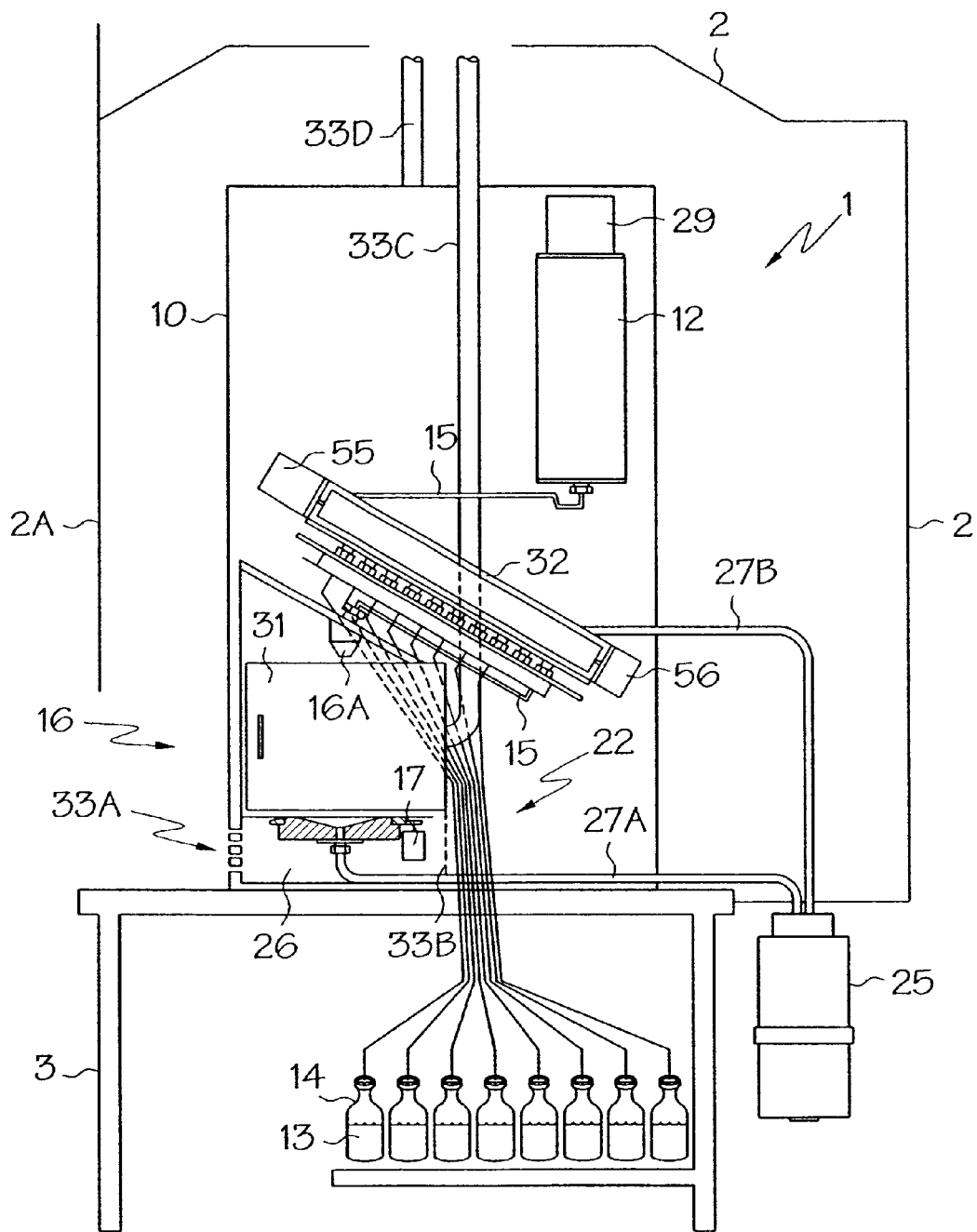
FIG. 2 is a schematic illustration of an enclosed fluid dispensing system of an embodiment of the present invention.

As shown in FIG. 2, a continuous fluid dispensing system 1 includes an enclosure 10, a pump 12 with a motor 29 (which is typically a stepper motor or servomotor), a fluid dispensing unit 16 a part of which includes a fluid dispensing nozzle 16A, and a fluid transport conduit 15. The exterior dimensions of fluid dispensing system 1 are such that the system can fit in a conventional laboratory fume hood 2 with sliding glass front door 2A, and on top of a stand 3, under which a plurality of fluid containers 14 can be stored. Passage of fluid injection lines 22 from enclosure 10 to stand 3 can be accomplished by mating apertures (not shown) on respective surfaces of the two. While in the preferred embodiment the pump 12 can be the aforementioned syringe pump, the inventors recognize that other types of pumps capable of precise metering of the desired fluid are equally valid substitutes. The space defined by fluid dispensing unit 16 is user-accessible via an opening in an upstanding wall (not shown) of enclosure 10, with such opening covered by a safety door 31 slidably mounted on the upstanding wall and positioned to block user access to fluid dispensing unit 16 and fluid dispensing nozzle 16A during operation. An optional safety interlock system (not shown) is added as a failsafe way to ensure fluid dispensing system 1 does not operate until safety door 31 is closed, thus preventing the inadvertent discharge of fluid 13 to the environment, the user, or both. Housing 32 is used to support the plurality of valves 18, which are used to fluid connect conduit 15 and pump 12 to dispensing unit 16 and dispensing nozzle 16A. Housing 32 is preferably placed at an incline to further ensure that any fluids in the main stream of conduit 15 drain, by the force of gravity, to the lowermost position, thus reducing the incidence of conduit wall buildup of droplets. Enclosure 10 further includes ventilation holes 33A and 33B, as well as exhaust tube 33C and exhaust stack 33D to facilitate venting of enclosure 10 and dispensing unit 16. Exhaust stack 33D can be further integrated into the ventilation duct (not shown) of fume hood 22, which can in turn be pumped away by facility ventilation systems (not shown). The ventilation enabled by ventilation holes 33A and 33B, exhaust tube 33C and exhaust stack 33D is useful in situations where fluid 13 emits noxious or corrosive fumes, which absent purging airflow through the enclosure 10, could present a hazard to users as well as hasten the degradation of exposed components.

Figure 3:
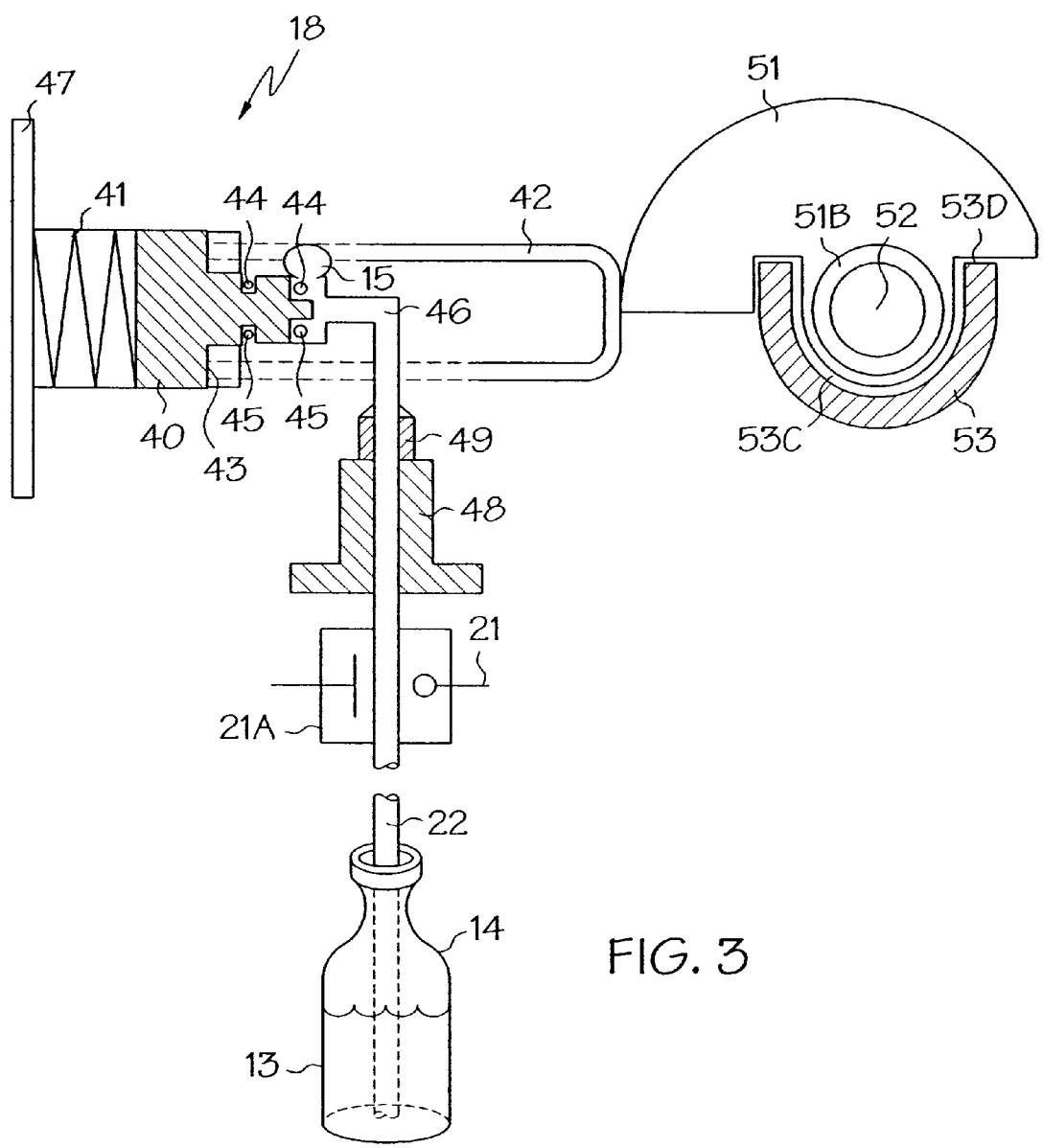
FIG. 3 is a schematic illustration of a valve arrangement according to an embodiment of the present invention.

Referring now to FIG. 3, one representative valve 18 of the plurality of valves 18 housed in housing 32 is shown. The valve 18 includes a valve stem 40 that is biased by a spring 41 in a closed position. To open valve 18, a pushrod actuator 42 is forced by cam 51 (described in more detail later) against a rear stop member 43 of valve stem 40, thus causing valve stem 40 to overcome the spring bias, and creating an open path for fluid 13 to be suctioned up by pump 12 to flow from container 14, through fluid injection line 22, and into conduit 15. O-rings 44 are placed in grooves 45 of valve stem 40 to provide leak-resistant sealing around valve inlet 46. Each of the valves 18 are mounted inside housing 32, as well as to cover plate 47. Container 14, which holds a supply of fluid 13, is situated vertically below valve 18 so that excess fluid could be gravity-fed back into the container 14. Flow sensor 21 is mounted on PCB 21A, which is designed to fit around the fluid injection line 22. The connection between container 14 and valve 18 is secured and sealed by gland nut 48 and ferrule 49. In a preferred embodiment, the containers 14 are bottles, and are constructed of a material that can withstand chemical attack from the fluid therein. Where the fluid reagents are corrosive (such as an acid), the fluid-exposed components, including tubes, lines, conduits, containers, seals and O-rings are made from glass, fluoroelastomers such as Viton®, perfluoroelastomers such as Kalrez®, or related material such as Teflon® or polytetrafluoroethylene (PTFE).

Figure 4:
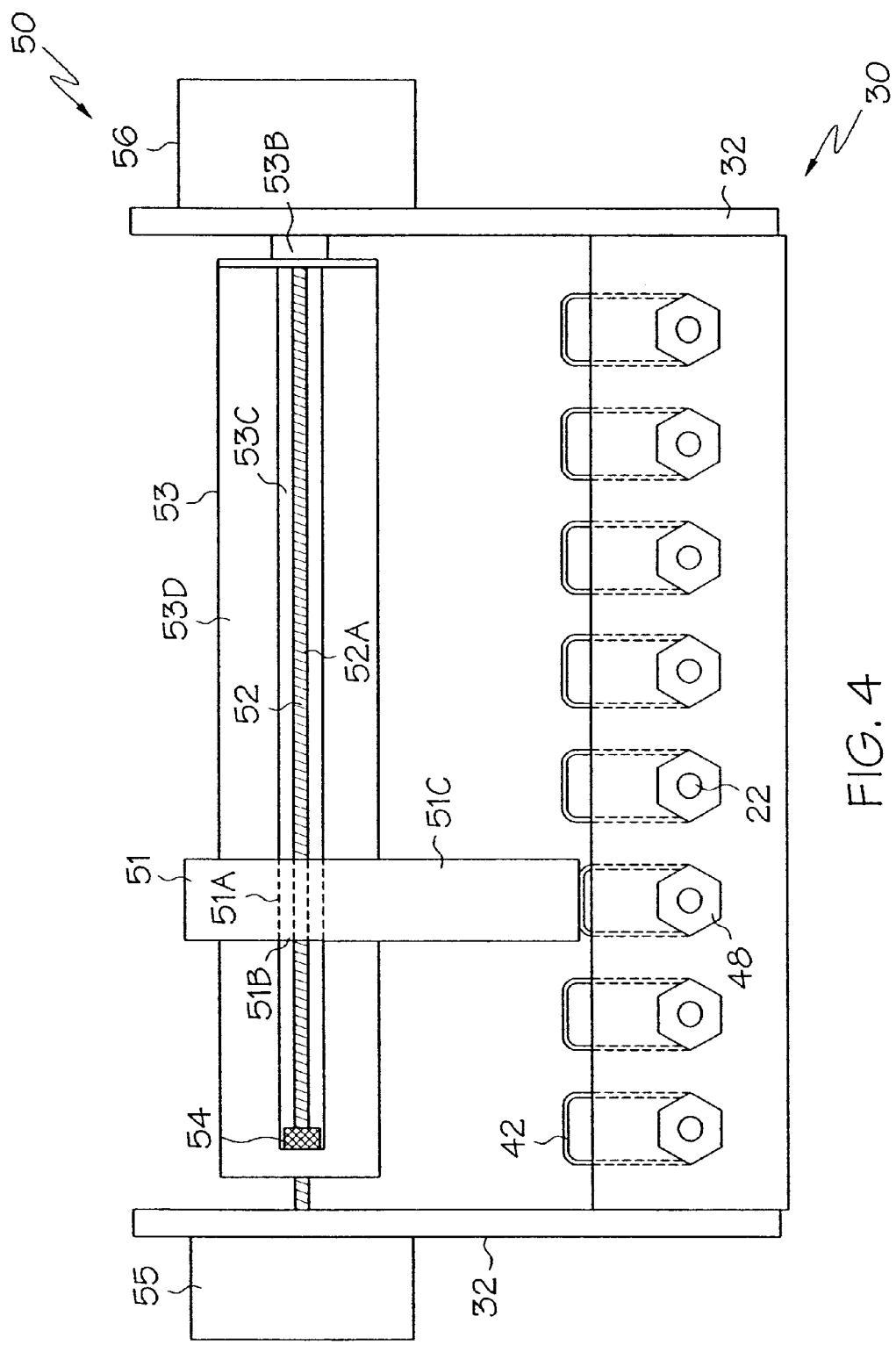
FIG. 4 is a top view of a flow control apparatus with housing, cam assembly and a plurality of valves.
Figure 5:
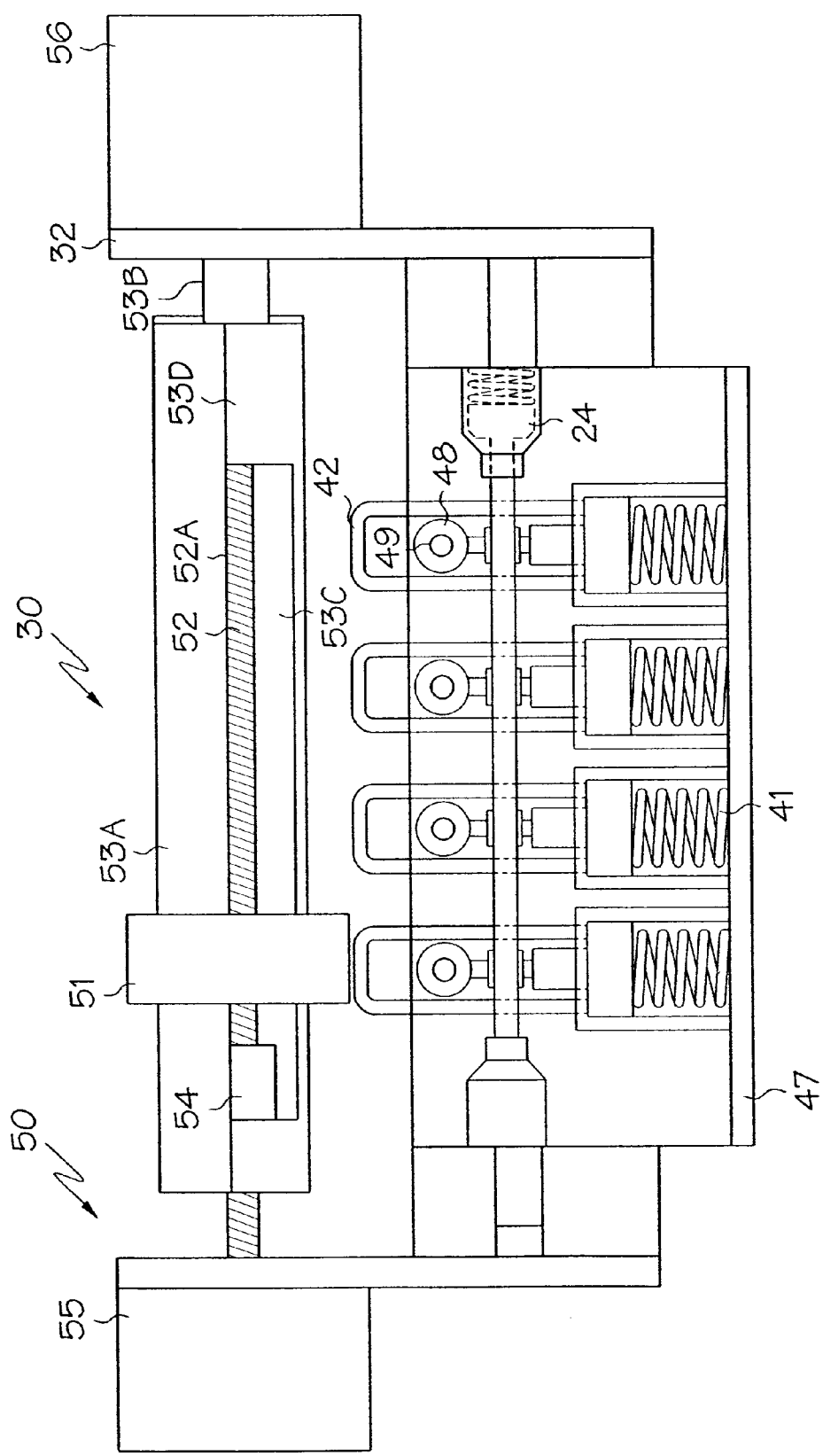
FIG. 5 is an isometric view highlighting the cam assembly of FIG. 4.

Referring now to FIGS. 4 and 5, flow control apparatus 30 includes housing 32, which contains a cam assembly 50 and a plurality of fluid injection valves 18, as well as bubble injection valve 19A, dispensant control valve 19B, and pressure relief valve 24. Each of the valves 18 are connected to an individual container 14, as well as to conduit 15. The valves 18 are preferably aligned in such a way so as to be readily accessible to being in mechanical communication with the single cam 51, either in a single line as shown, or in dual parallel lines with the cam 51 spaced parallel to and equidistant between them (not shown). Once aligned, the cam 51 is then rotated so that its inherent eccentricity will engage the valve's actuator 42, thereby forcing a change in the amount of fluid allowed to flow through the valve 18. By this arrangement, the single cam 51 can control the movement of every valve, one at a time by responding to motor-driven signals from microprocessor-based controller 23.

Cam assembly 50 comprises cam 51, shaft 52, rotational member 53, bushing 54, first motor 55 and second motor 56. By translating up and down the length of the shaft 52, cam 51 can be positioned in relation to any one of the valves 18. Then, by rotating, cam 51 can actuate any one of the valves 18 according to predetermined needs for a particular fluid. Preferably, shaft 52 is a smaller diameter generally cylindrical cross section lead screw shaft, which imparts translational movement to cam 51. In addition to being mounted to shaft 52, cam 51 is mounted to the rotational member 53, which is of larger diameter than shaft 52. In the present context, when one object is "mounted" to another, it means that the objects are in direct, uninterrupted, contiguous mechanical communication with one another, with no other components in between. Thus, one can either be pivotally or rotatably attached to the other (such as through a hinge, bearing or pivot), or simply supported on the other (such as in an unattached, resting relationship), or the objects can be conventionally attached to each other (such as by bolting, gluing, screwing, welding, soldering, and the like). Rotational member 53, which includes a larger diameter cam engaging section 53A, smaller diameter cam driver engaging section 53B, hollow center section 53C and generally planar surface 53D, imparts rotational movement to cam 51. The axes of rotation of the cam 51, shaft 52 and rotational member 53 are coaxial, with shaft 52 disposed inside the hollow center section 53C of rotational member 53, terminating in a receiving cup (not shown) at a distal end of hollow center section 53C which, along with bushing 54 disposed between shaft 52 and rotational member 53 at a proximal end of hollow center section 53C, maintains proper alignment between the shaft 52 and rotational member 53. Specifically referring to FIG. 3, wherein shaft 52 and rotational member 53 are viewed looking down their mutual axis of rotation, and with bushing 54 removed for clarity, rotational member 53 defines a truncated cylindrical cross section, revealing a generally planar surface 53D that engages cam 51, while simultaneously permitting uninhibited connection between shaft 52 and cam aperture 51B, where the size of aperture 51B is shown exaggerated and without helical-shaped threads 52A for clarity. The combined translational and rotational movement of cam 51 is referred to as motion in two degrees of freedom. As used herein, the term "degrees of freedom" coincide with the convention used in solid or continuum mechanics, where a continuous medium in Euclidean space can experience a total of six degrees of freedom of motion: three translational (along each of the x, y and z axes in a Cartesian system), and three rotational along each of the same three axes.

Shaft 52 is aligned with rotating member 53 by bushing 54. Shaft 52, rotational member 53, first motor 55 and second motor 56 are conventionally mounted to housing 32, while bushing 54 is mounted to both shaft 52 and rotational member 53. Translation movement of cam 51 is achieved by using the first motor 55, disposed at one end of housing 32, to turn shaft 52. Helical-shaped threads 52A extend substantially between opposing ends of the outer surface of shaft 52, and engage inner surface 51A of an aperture 51B in cam 51, which is complementary threaded. Once cam 51 is put into aligned relationship with pushrod 42 of a selected valve 18, rotational movement of cam 51 can be achieved by using the second motor 56 disposed at the opposing end of housing 32 to turn rotational member 53. Upon rotation, eccentric portion 51C of cam 51 comes into contact with pushrod 42, forcing it to open or close valve 18 to its desired position, which, in turn, alters the amount of flow through fluid injection line 22, which is mounted in gland nut 48 and ferrule 49. While the configuration of FIGS. 4 and 5 depict the use of two motors, one for each of rotational and translational movement, it is noted that a single motor could be used to provide both forces through, for example, a clutch or gearing arrangement between the motor, shaft and rotational member. Regardless of the number of motors used to provide cam 51 movement, it is noted that conventional stepper or servomotors provide reliable, inexpensive power. In addition, while the embodiment depicted in FIG. 5 notionally includes four valves, it is readily appreciated that the present invention can accommodate any number of valves, limited only by the needs of the end use application.

Figure 6:
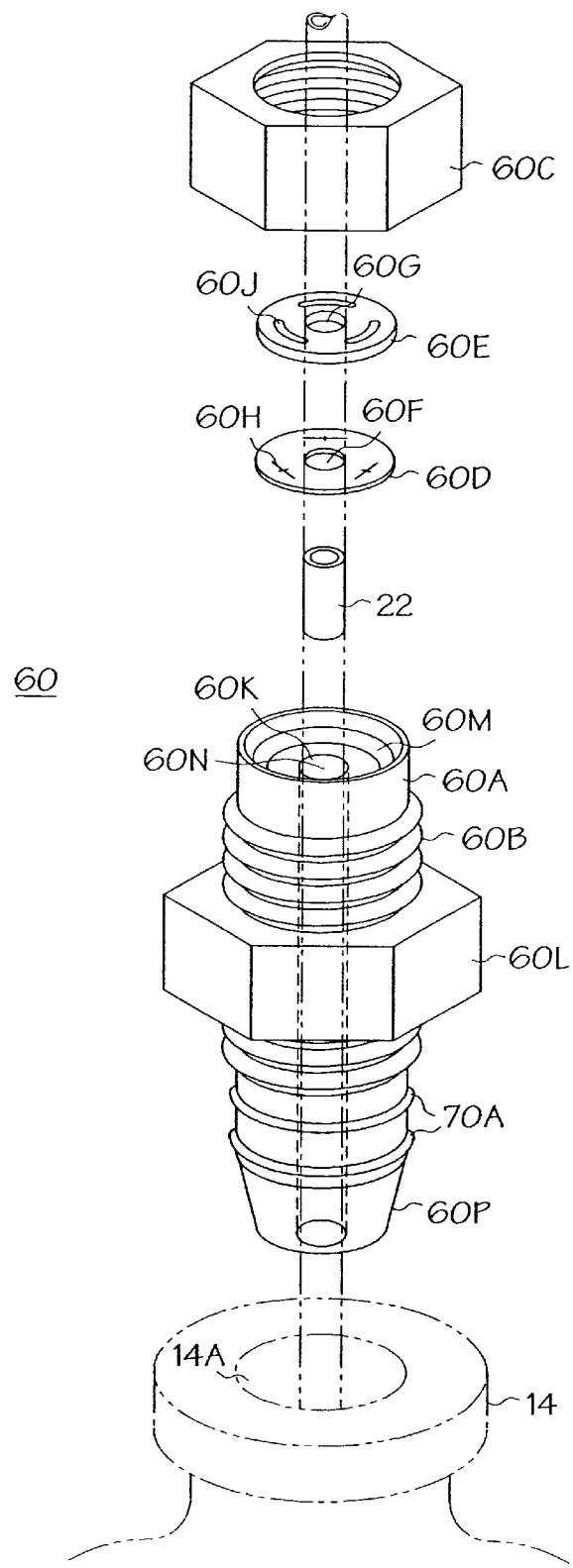
FIG. 6 is an illustration of a reagent fluid containment bottle with a stopper capping mechanism in accordance with an embodiment of the present invention.

Referring now to FIG. 6, capping mechanism 60 acts as a stopper to be placed in the aperture 14A of container 14 to allow the insertion and removal of fluid from container 14 while simultaneously limiting exposure of the fluid (not shown) disposed therein to the ambient environment, in order to inhibit spillage of the fluid or release of vapors. Capping mechanism 60 is made up of a body 60A, with threads 60B disposed on the outer surface thereof to engage a complementary threaded inner surface of top 60C and body disengaging nut 60L. Vent membrane 60D and membrane plate 60E, each with substantially centrally disposed channels 60F, 60G, respectively are axially-aligned disk-like members that fit in chamber 60K disposed in the top of body 60A such that they rest on ledge 60M. Vent membrane 60D, which is typically made of a compliant elastic material, such as Viton®, includes a plurality of slits 60H disposed circumferentially about channel 60F. These slits 60H can open in response to pressure differentials across the surface of vent membrane 60D. Recesses 60J, substantially axially aligned with slits 60H, permit fluid communication between chamber 60K (which itself is in fluid communication with the gaseous region inside container 14 above the liquid line 13A by virtue of passage 60N being of slightly greater diameter than fluid injection line 22) and the ambient environment. Top 60C, through threaded engagement with threads 60B, secures vent membrane 60D and membrane plate 60E in an axially fixed position relative to chamber 60K. Body disengaging nut 60L, with internal threads (not shown) to engage threads 60B of body 60A, is used to gently but firmly remove capping mechanism 60 from aperture 14A. Fluid injection line 22 can frictionally engage channels 60F and 60G to secure fluid injection line 22 in place. Passage 60N is axially disposed in body 60A and extends from the bottom of the chamber 60K through to the bottom plug portion 60P, thereby allowing gas in container 14 to be vented through slits 60H and recesses 60J upon return of liquid through fluid injectant line 22 to container 14. During aspiration of liquid into fluid injectant line 22 as a result of suction applied to fluid injectant line 22, air enters the container 14 through slits 60H, recesses 60J, chamber 60K, and passage 60N. Note that a second membrane plate (not shown) identical to membrane plate 60E could be situated under vent membrane 60D to create a stacked, sandwich structure. Such a configuration could be included in the event that additional support of vent membrane 60D is desired. The portion of capping mechanism 60 designed to fit inside the aperture can optionally include one or more O-ring grooves (not shown) with inserted O-rings 70.

Alternatively, for containers 14 which have external threads on the neck of the bottle (not shown), the capping arrangement previously described can be simplified; in this case including solely an oversized variant (not shown) of threaded top 60C with a smaller opening (not shown) sized to accommodate the fluid injection line 22, membrane plate 60E and vent membrane 60D. The internal threads on the oversized top would engage the external threads on the neck of the container 14, while an arrangement of vent membrane 60D and one or more membrane plates 60E can be axially disposed between the threaded top and the top of the neck of container 14. Fluid is transferred either into or out of the container 14 in the same manner as above. As previously discussed, two membrane plates 60E may be used to sandwich a single vent membrane 60D in this arrangement.

Figure 7:
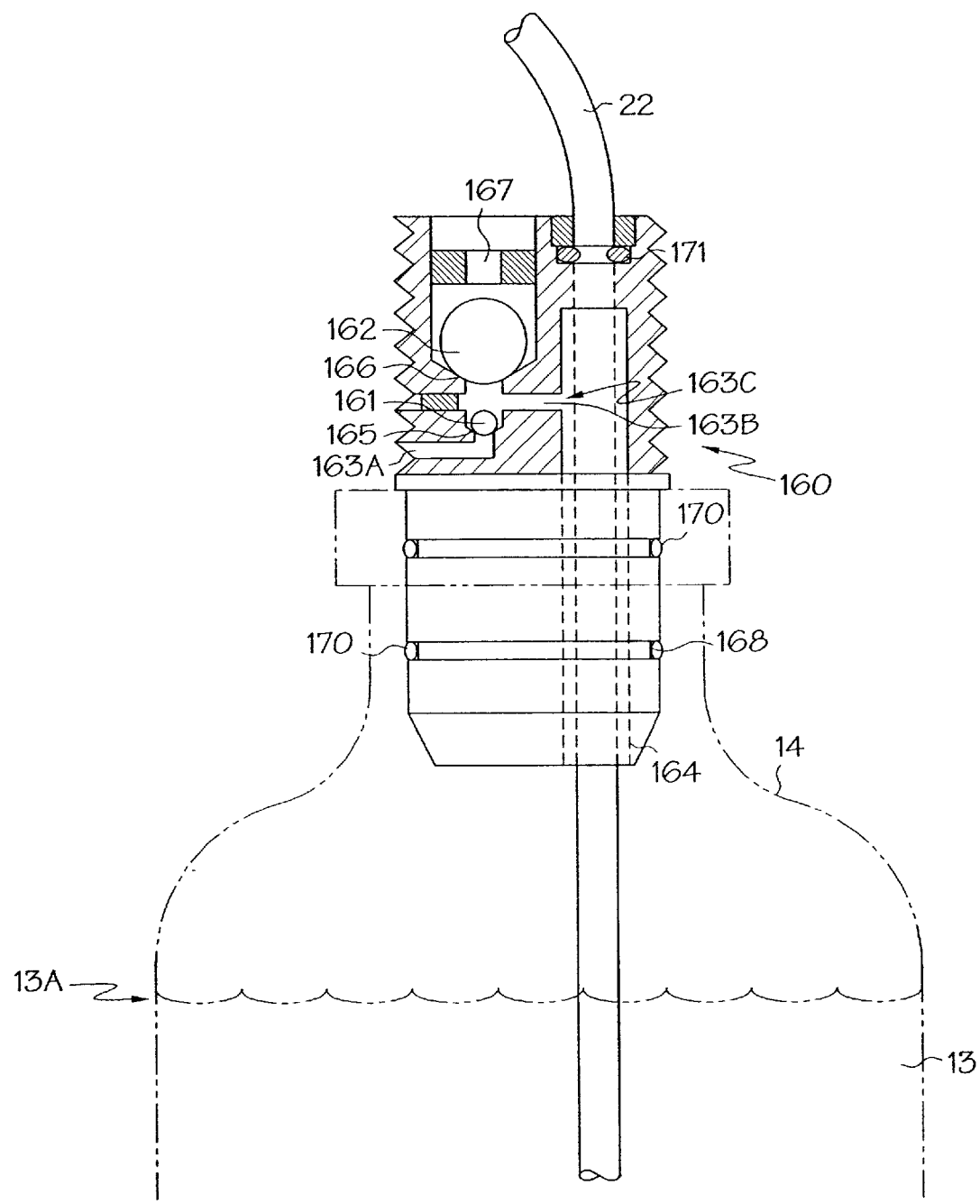
FIG. 7 is an illustration of an alternate embodiment stopper capping mechanism.

Referring now to FIG. 7, an alternate embodiment of the capping mechanism shown in FIG. 6 is shown, with capping mechanism 160 and spherical-shaped stopper members 161, 162, which together comprise a two-way vent. During the suction phase, where fluid 13 is being dispensed from container 14 through fluid injection line 22, a partial vacuum is created in fluid injection line 22 which, due to it being in fluid communication with venturi 163C through fluid 13, the gaseous region above the liquid line 13A, and the gap between fluid injection line 22 and access tube 164 in capping mechanism 160, draws in higher pressure ambient air from outside the container 14. For ambient air to reach venturi 163C, it is necessary that it push smaller sphere 161 out of the way. The weight of smaller sphere 161 is such that the incoming air is of sufficient pressure to cause smaller sphere 161 to raise up off of small seating throat 165, thus admitting air into container 14 via passages 163A and 163B and venturi 163C. The incoming air, which is in fluid communication with the gaseous region inside container above liquid line 13A through gaps between fluid injection line 22 and access tube 164, exerts pressure on fluid 13, pushing it up and into fluid injection line 22. When the pressure is equalized, smaller sphere 161 reseats on small seating throat 165. During the fluid input phase, the process is reversed. Increased pressure in the fluid injection line 22 forces smaller sphere 161 even more forcefully against small seating throat 165. In addition, the higher pressure overcomes the gravitational force on larger sphere 162, and lifts it off large seating throat 166, placing a vent port 167 (and the lower pressure ambient air) in fluid communication with the higher pressure gaseous region situated above liquid line 13A in container 14. Larger sphere 162 is massive enough so as to positively reseat upon return to pressure equilibrium between container 14 and the ambient environment, and in so doing, reduces the likelihood that the enclosed fluid will evaporate. It is also noted that smaller sphere 161 and larger sphere 162 could both have their seating enhanced by the addition of O-rings (not shown). Ambient conditions are defined as those which exist outside of a fluid's primary container, and typically include pressures and temperatures found in normal industrial or laboratory settings. Thus, if the fluid resides in a bottle, the environment outside the bottle is considered "ambient", even if the bottle is itself contained within another, larger enclosure. The reduction in the likelihood of evaporation is important for fluids with high vapor pressures, such as acids and solvents. The portion of stopper 160 above the aperture of the container 14 can optionally have grooved outer surface, to engage a threaded top (not shown for clarity). The top facilitates easier, safer removal; by screwing the top down, it interacts with the grooves in capping mechanism 160 to gently, but smoothly lift capping mechanism 160 out of the container aperture, thereby preventing a recoil or snapping action when the capping mechanism 160 finally disengages from the container 14. As with the previous embodiment, the portion of capping mechanism 160 beneath the aperture can optionally include O-ring grooves 168. Their inclusion, in conjunction with inserted O-rings 170, also helps prevent the sudden, often violent snapping action of the container upon removal of capping mechanism 160. Fluid injection line 22 is friction fitted into the uppermost portion of capping mechanism 160, with sealing provided by an additional set of O-rings 171 disposed near the top.

Having described the invention in detail and by reference to the aspects thereof, it will be apparent that modifications and variations are possible without departing from the scope of the invention which is defined in the appended claims:

What is claimed is:

1. A fluid dispensing system comprising:
    at least one pump for metering precise quantities of fluid to be dispensed;
    a plurality of fluid injection lines for transporting said fluid to be dispensed;
    a plurality of valves each of which are disposed in one of said plurality of fluid injection lines, each of said plurality of valves including a valve actuator, wherein said plurality of fluid injection lines can be in fluid communication with a plurality of containers for dispensing fluid, such that said each of said plurality of valves controls the flow of said fluid through one of said plurality of fluid injection lines;
    at least one valve actuator engaging member in mechanical communication with at least one of said valve actuators;
    a fluid transport conduit in fluid communication with said at least one pump and said plurality of fluid injection lines;
    a flow detection system disposed adjacent said plurality of fluid injection lines, said flow detection system comprising:
        at least one detector; and
        a controller in electrical communication with said detector, said plurality of valves and said at least one pump such that upon detection and comparison of a flow variation, said controller sends signals to at least one of said at least one pump or said plurality of valves to control the flow of fluid;
    a dispensing unit operatively responsive to said fluid transport conduit so as to accept fluid therefrom; and
    a capping mechanism adapted to be disposed in an aperture in each of said plurality of containers, said capping mechanism comprising:
        a body;
        at least one recess disposed in said body to define an aperture therein to receive a fluid injection line therethrough; and
        at least one valve coupled to said body.

2. A fluid dispensing system according to claim 1, further comprising a fluid contained within said system.

3. A fluid dispensing system according to claim 1, wherein said capping mechanism further comprises:
    at least one elastic vent member comprising:
        at least one slit disposed therein, said slit responsive to pressure differentials between the inside and outside of said container; and
        at least one channel disposed therein, said channel capable of receiving a fluid injection line therethrough; and
    at least one membrane plate comprising:
        at least one recess disposed therein, said recess in substantial axial alignment with said at least one slit; and
        at least one channel disposed therein, said channel capable of receiving a fluid injection line therethrough.

4. A fluid dispensing system according to claim 1, wherein said capping mechanism further comprises:
    a plurality of passages disposed in said body and configured to permit selective fluid communication between the inside and outside of said container; and
    a plurality of generally spherical stoppers, each seatably disposed within one of said passages in said body, each of said stoppers seatably responsive to said pressure differential, such that, upon exposure to said pressure differential, said plurality of generally spherical stoppers change their seating arrangement.

5. A fluid dispensing system according to claim 1, wherein said at least one detector is ultrasonic.

6. A fluid dispensing system according to claim 1, wherein said at least one detector is optical.

7. A fluid dispensing system according to claim 6, wherein said at least one optical detector is an IR detector.

8. A fluid dispensing system according to claim 2, wherein said fluid to be dispensed is a neutralizer with integral dye indicator.

9. A fluid dispensing system according to claim 1, further comprising an enclosure to house at least one of said at least one pump, said plurality of fluid injection lines, said plurality of valves, said at least one valve actuator, said fluid transport conduit, said flow detection system or said dispensing unit.

10. A fluid dispensing system according to claim 9, further including a door disposed on said enclosure to prevent fluid spillage from escaping said enclosure.

11. A fluid dispensing system according to claim 1, further comprising a bubble injection mechanism configured to introduce an immiscible fluid into said conduit.

12. A fluid dispensing system according to claim 11, wherein said immiscible fluid is air.

13. A fluid dispensing system according to claim 1, further comprising a pusher fluid selectively introduced into said fluid transport conduit to force the flow of said fluid to be dispensed through said fluid transport conduit.

14. A fluid dispensing system according to claim 1, wherein said capping mechanism further comprises at least one recess disposed in a downwardly-projecting outer surface thereof, said at least one recess configured to receive an O-ring therein to facilitate sealing contact between said container and said capping mechanism.

15. A fluid dispensing system according to claim 5, wherein said plurality of passages are configured such that, upon removal of said fluid from said container, a first of said generally spherical stoppers that is disposed in one of said passages is unseated, thereby facilitating pressure equalization between the inside and the outside of said container.

16. A fluid dispensing system according to claim 5, wherein said plurality of passages are configured such that, upon introduction of said fluid into said container, a second of said generally spherical stoppers that is disposed in one of said passages is unseated, thereby facilitating pressure equalization between the inside and the outside of said container.

17. A fluid dispensing system according to claim 1, wherein said generally cylindrical body of said capping mechanism comprises at least one threaded groove disposed on an outer surface thereof, further wherein said top comprises a surface configured to threadably engage said at least one threaded groove.

18. A device according to claim 1, further comprising a seal disposed between said body and said container.

19. A device according to claim 1, wherein said at least one valve of said capping mechanism is configured to assume an open position when suction is applied to said container and a closed position when suction is removed from said container.

20. A device according to claim 19, wherein said at least one valve of said capping mechanism comprises at least one additional valve, said at least one additional valve configured to assume an open position when fluid is introduced to said container and a closed position when fluid is not being introduced into said container.

21. A device according to claim 4, wherein said fluid to be dispensed is an acid, solvent or acid neutralizer.

22. A fluid dispensing system according to claim 1, wherein said at least one valve of said capping mechanism is operatively responsive to a pressure differential across said valve.

23. A fluid dispensing system according to claim 13, wherein said pusher fluid is a gas.

24. A fluid dispensing system according to claim 13, further comprising a filter disposed in said fluid injection lines to provide fluid damping.

25. A method of preparing metallurgical etchants, comprising the steps of:
placing at least one fluid container with a fluid to be dispensed in operative communication with at least one valve;
disposing a capping mechanism in an aperture of said container, said capping mechanism comprising:
a body;
at least one recess disposed in said body to define an aperture therein to receive a fluid injection line therethrough; and
at least one valve coupled to said body;
arranging a valve actuator to be in mechanical communication with said at least one valve;
placing a fluid injection line in fluid communication with said at least one valve such that said fluid injection line is also in operative communication with said at least one fluid container;
placing a fluid transport conduit in fluid communication with said fluid injection line;
placing at least one pump for metering precise quantities of said fluid to be dispensed in fluid communication with said fluid transport conduit, thereby establishing fluid communication between said at least one pump and said at least one fluid container;
selectively introducing said fluid to be dispensed into said fluid transport conduit to force said fluid to be dispensed therethrough;
monitoring the flow of said fluid to be dispensed through said fluid injection line with a flow detection system, said flow detection system comprising:
at least one detector placed in sensor communication with said fluid injection line; and
a controller in electrical communication with said detector, said at least one valve and said at least one pump such that upon detection and comparison of a flow variation, said controller sends signals to at least one of said at least one pump or said at least one valve to control the flow of said fluid to be dispensed;
controlling the opening or closing of said at least one valve in response to a predetermined process condition, said controlling accomplished by:
receiving an input from said controller; and
sending a control signal from said controller to said valve actuator, thereby forcing engagement between said valve actuator and said at least one valve to an extent dictated by said control signal such that said at least one valve adjusts a flow of said fluid to be dispensed therethrough; and
operating said at least one pump to move a predetermined amount of said fluid to be dispensed from said at least one fluid container, through said at least one valve, said fluid injection line, said fluid transport conduit, and into a dispensing unit in fluid communication with said fluid transport conduit so as to accept fluid therefrom.

26. A method according to claim 25, wherein said fluid to be dispensed is an acid, solvent, acid neutralizer or combination thereof.

27. A method according to claim 25, wherein said fluid to be dispensed is a neutralizer with integral dye indicator.

28. A method according to claim 25, comprising the additional steps of:
configuring a bubble injection mechanism to selectively introduce an immiscible fluid into said conduit;
introducing said immiscible fluid into said fluid transport conduit once said fluid has been dispensed into said dispensing unit; and
purging said fluid transport conduit with said immiscible fluid.

29. A method according to claim 25, comprising the additional step of introducing a pusher fluid into said fluid transport conduit to force the flow of said fluid to be dispensed through said fluid transport conduit.

30. A method according to claim 25, wherein said capping mechanism further comprises
a top engaged with said container to provide for selective removal of said body from said container.

31. A method according to claim 30, wherein said capping mechanism further comprises at least one recess disposed in a downwardly-projecting outer surface thereof, said at least one recess configured to receive an O-ring therein to facilitate sealing contact between said container and said capping mechanism.

32. A method of preparing metallurgical etchants according to claim 25, wherein said at least one valve of said capping mechanism is operatively responsive to a pressure differential across said valve.

33. A fluid dispensing system comprising:
at least one pump for metering precise quantities of fluid to be dispensed;
a plurality of fluid injection lines for transporting said fluid to be dispensed;
a plurality of valves each of which are disposed in one of said plurality of fluid injection lines, each of said plurality of valves including a valve actuator, wherein said plurality of fluid injection lines can be in fluid communication with a plurality of containers for dispensing fluid, such that said each of said plurality of valves controls the flow of said fluid through one of said plurality of fluid injection lines;
at least one valve actuator engaging member in mechanical communication with at least one of said valve actuators;
a fluid transport conduit in fluid communication with said at least one pump and said plurality of fluid injection lines;
a flow detection system disposed adjacent said plurality of fluid injection lines, said flow detection system comprising:
at least one detector; and a controller in electrical communication with said detector, said plurality of valves and said at least one pump such that upon detection and comparison of a flow variation, said controller sends signals to at least one of said at least one pump or said plurality of valves to control the flow of fluid;

a dispensing unit operatively responsive to said fluid transport conduit so as to accept fluid therefrom; and a bubble injection mechanism configured to introduce an immiscible fluid into said conduit.

* * * * *

UNITED STATES PATENT AND TRADEMARK OFFICE
CERTIFICATE OF CORRECTION

PATENT NO.   : 6,689,621 B2
DATED        : February 10, 2004
INVENTOR(S)  : Merten et al.

It is certified that error appears in the above-identified patent and that said Letters Patent is hereby corrected as shown below:

Column 11,
Line 19, reads as "fume hood 22", should read -- fume hood 2 --.

Column 13,
Line 64, reads as "O-rings 70", should read -- O-rings 70A --.

Signed and Sealed this

Sixth Day of July, 2004

JON W. DUDAS
*Acting Director of the United States Patent and Trademark Office*